(12) United States Patent
Venkatesh

(10) Patent No.: US 6,558,699 B2
(45) Date of Patent: May 6, 2003

(54) HIGH DRUG LOAD IMMEDIATE AND MODIFIED RELEASE ORAL DOSAGE FORMULATIONS AND PROCESSES FOR THEIR MANUFACTURE

(75) Inventor: Gopadi M. Venkatesh, Blue Brook, OH (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/021,335

(22) Filed: Dec. 12, 2001

(65) Prior Publication Data

US 2002/0098241 A1 Jul. 25, 2002

Related U.S. Application Data

(63) Continuation of application No. 09/842,760, filed on Apr. 26, 2001, now abandoned, which is a continuation of application No. 09/554,257, filed as application No. PCT/US98/24502 on Nov. 17, 1998, now abandoned.
(60) Provisional application No. 60/065,918, filed on Nov. 17, 1997.

(51) Int. Cl.[7] .............................. A61K 9/20; A61K 9/22; A61K 9/26
(52) U.S. Cl. ........................ 424/464; 424/468; 424/469; 424/465; 424/470
(58) Field of Search .................................. 424/464, 468, 424/469, 465, 470

(56) References Cited

U.S. PATENT DOCUMENTS

| 4,444,769 A | * | 4/1984 | Blume et al. ................ 424/246 |
| 4,610,870 A | * | 9/1986 | Jain et al. ..................... 424/19 |
| 5,185,351 A | * | 2/1993 | Finkelstein et al. ......... 514/341 |
| 5,656,650 A | * | 8/1997 | Weinstock .................. 514/396 |
| 5,684,029 A |   | 11/1997 | Narr et al. |

FOREIGN PATENT DOCUMENTS

| WO | WO-97/36874 A1 | * | 10/1997 |
| WO | WO-99/00383 A1 | * | 1/1999 |

* cited by examiner

Primary Examiner—Thurman K. Page
Assistant Examiner—Rachel M. Bennett
(74) Attorney, Agent, or Firm—Laura K. Madden; Mary E. McCarthy; Charles M. Kinzig

(57) ABSTRACT

This invention relates to high drug load granulation of (E)-α-[2-n-butyl-1-[(4-carboxyphenyl)methyl]-1H-imidazol-5-yl]methylene-2-thiophenepropionic acid in the anhydrous form, a process for its production, compositions containing the compound and methods of using the compound to block angiotensin II receptors and to treat hypertension, congestive heart failure and renal failure.

21 Claims, 3 Drawing Sheets

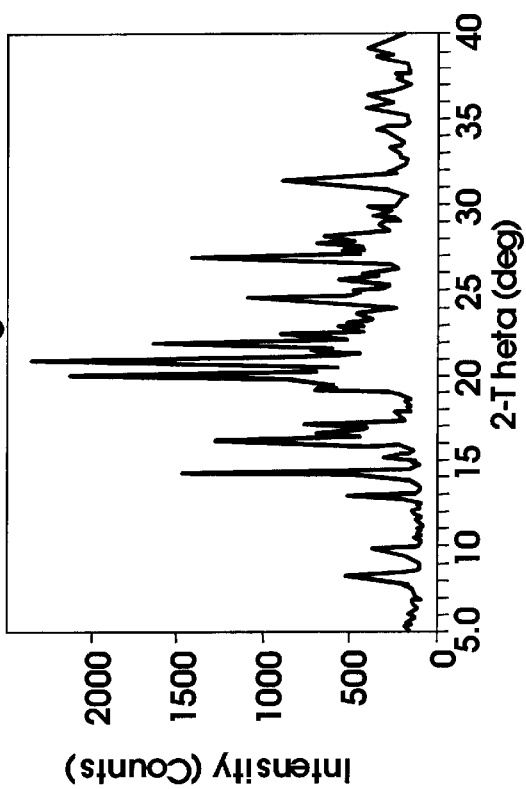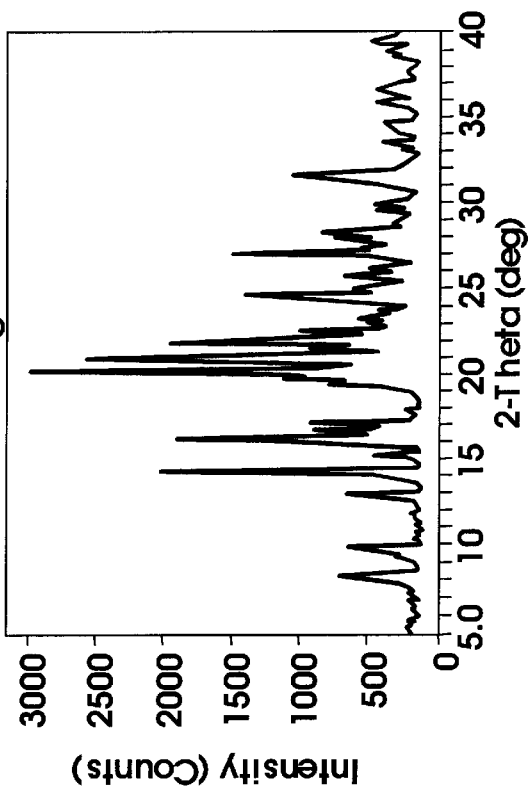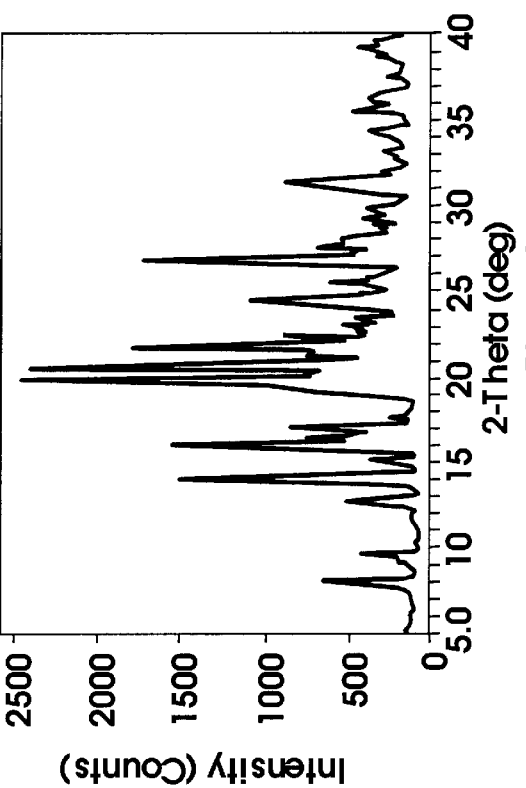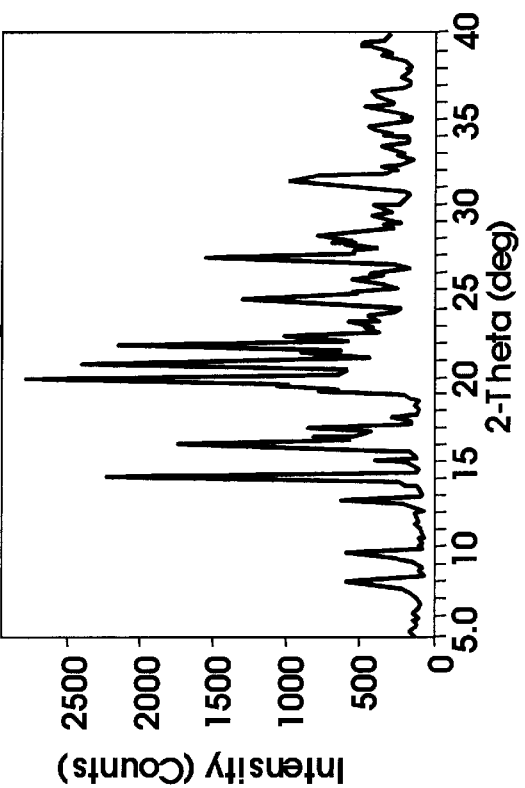

HIGH DRUG LOAD IMMEDIATE AND MODIFIED RELEASE ORAL DOSAGE FORMULATIONS AND PROCESSES FOR THEIR MANUFACTURE

This is a continuation of application Ser. No. 09/842,760 filed Apr. 26, 2001 now abandoned which is a cont. of 09/554,257, filed May 11, 2000 now abandoned which is a International Application No. PCT/US98/24502, filed Nov. 17, 1998, which claims priority to U.S. Provisional Application No. 60/065,918, filed Nov. 17, 1997.

FIELD OF THE INVENTION

This invention relates to high drug load formulations, processes for preparing these formulations, and methods of using high drug load formulations in the treatment of certain disease states in mammals, in particular man. Specifically, the present invention relates to the use of anhydrous (E)-α-[2-n-butyl-1-[(4-carboxyphenyl)methyl]-1H-imidazol-5-yl]methylene-2-thiophenepropionic acid in the preparation of high drug load immediate and modified release tablet formulations, wet or dry granulation processes for preparing high drug load granules, oral dosage forms containing these high drug load granules, and methods of using high drug load formulations of (E)-α-[2-n-butyl-1-[(4carboxyphenyl)methyl]-1H-imidazol-5-yl]methylene-2-thiophenepropionic acid to block angiotensin II (AII) receptors and to treat hypertension, congestive heart failure and renal failure.

BACKGROUND OF THE INVENTION

The compound, (E)-α-[2-n-butyl-1-[(4carboxyphenyl)methyl]-1H-imidazol-5-yl]methylene-2-thiophenepropionic acid, is known by the name "eprosartan" and is the subject of U.S. Pat. No. 5,185,351 (the '351 patent), issued Feb. 9, 1993. This patent discloses a process for making the anhydrous form of (E)-α-[2-n-butyl-1-[(4-carboxyphenyl)methyl]-1H-imidazol-5-yl]methylene-2-thiophenepropionic acid and its methane sulfonate salt. Additionally, the '351 patent discloses conventional techniques for formulating (E)-α-[2-n-butyl-1-[(4-carboxyphenyl)-methyl]-1H-imidazol-5-yl]methylene-2-thiophenepropionic acid. This compound is claimed to have utility in blocking angiotensin II receptors and to be useful in the treatment of hypertension, congestive heart failure and renal failure.

International Application Number PCT/US97/04877, filed Mar. 26, 1997. relates to a novel dihydrated form of (E)-α-[2-n-butyl-1-[(4-carboxyphenyl)methyl]-1H-imidazol-5-yl]methylene-2-thiophenepropionic acid monomethanesulfonate, in particular, in pharmaceutical compositions for the treatment of diseases in which blockade of angiotensin II receptors is indicated, for example, in the treatment of hypertension, congestive heart failure and renal failure. This form of (E)-α-[2-n-butyl-1-[(4-carboxyphenyl)methyl]-1H-imidazol-5-yl]methylene-2-thiophene-propionic acid monomethanesulfonate is produced during the wet granulation of the anhydrous form of (E)-α-[2-n-butyl-1-[(4-carboxyphenyl)-methyl]-1H-imidazol-5-yl]methylene-2-thiophenepropionic acid monomethanesulfonate.

Surprisingly, it has been found that anhydrous (E)-α-[2-n-butyl-1-[(4-carboxyphenyl)methyl]-1H-imidazol-5-yl]methylene-2-thiophenepropionic acid does not form a hydrate during wet granulation. This discovery has allowed for the preparation of reduced size, high drug load tablets. This is particularly important when formulating eprosartan for commercial use.

SUMMARY OF THE INVENTION

The present invention provides high drug load formulations of anhydrous (E)-α-[2-n-butyl-1-[(4-carboxyphenyl)methyl]-1H-imidazol-5-yl]methylene-2-thiophenepropionic acid and oral solid dosage forms of this compound for the treatment of diseases in which blockade of angiotensin II receptors is indicated, for example, in the treatment of hypertension, congestive heart failure and renal failure. These high drug load formulations are in immediate or modified release oral solid dosage forms.

The present invention also provides processes for preparing high drug load tablet formulations of (E)-α-[2-n-butyl-1-[(4-carboxyphenyl)methyl]-1H-imidazol-5-yl]-methylene-2-thiophenepropionic acid by dry or wet granulation of the anhydrous form of (E)-α-[2-n-butyl-1-[(4-carboxyphenyl)methyl]-1H-imidazol-5-yl]methylene-2-thiophenepropionic acid in the presence of pharmaceutically acceptable excipients.

BRIEF DESCRIPTION OF THE FIGURES

FIGS. 1(A), 2(A) and 3(A) show, respectively, the thermogravimetric analysis (TGA), the differential scanning calorimetric (DSC) thermogram and the powder X-ray diffraction (XRD) pattern of the free base of anhydrous (E)-α-[2-n-butyl-1-[(4-carboxyphenyl)methyl]-1H-imidazol-5-yl]methylene-2-thiophenepropionic acid.

Figure 1A:
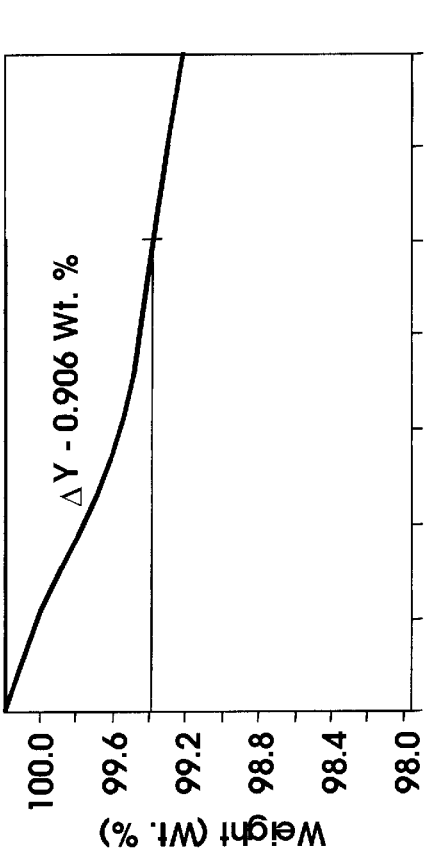
Figure 2A:
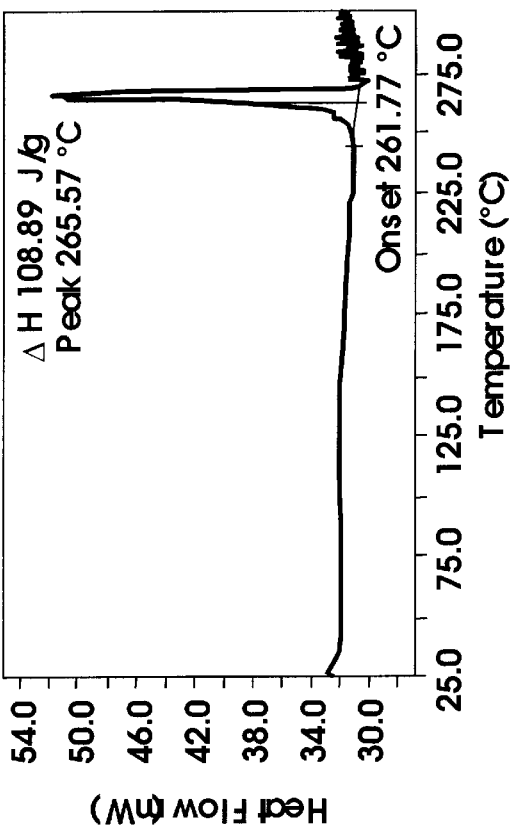

The anhydrous form of (E)-α-[2-n-butyl-1-[(4-carboxyphenyl)methyl]-1H-imidazol-5-yl]methylene-2-thiophenepropionic acid exhibits a single thermal event, a melting endotherm at about 269° C. associated with a weight loss, suggesting that melting is followed by decomposition of the drug substance (FIG. 2A). No significant weight loss prior to melting is observed in its TGA (thermogravimetric analysis) [FIG. 1(A)], suggesting that this compound does not contain significant quantities of surface adsorbed water and/or residual solvents. The powder X-ray diffraction pattern [FIG. 3(A)] exhibits characteristic diffraction lines corresponding to 2θ values of 8.15, 9.74, 14.20, 16.09, 17.09, 19.99, 20.71, 21.81, 22.38, 24.49, 26.84 and 31.39 degrees.

FIGS. 1B–D, 2B–D and 3B–D show, respectively, the thermogravimetric analysis (TGA), the differential scanning calorimetric (DSC) thermogram and the powder X-ray diffraction (XRD) patterns for the granulations of the free base of anhydrous (E)-α-[2-n-butyl-1-[(4-carboxyphenyl)methyl]-1H-imidazol-5-yl]methylene-2-thiophenepropionic acid with different binders and binder-diluent combinations.

Figure 1B:
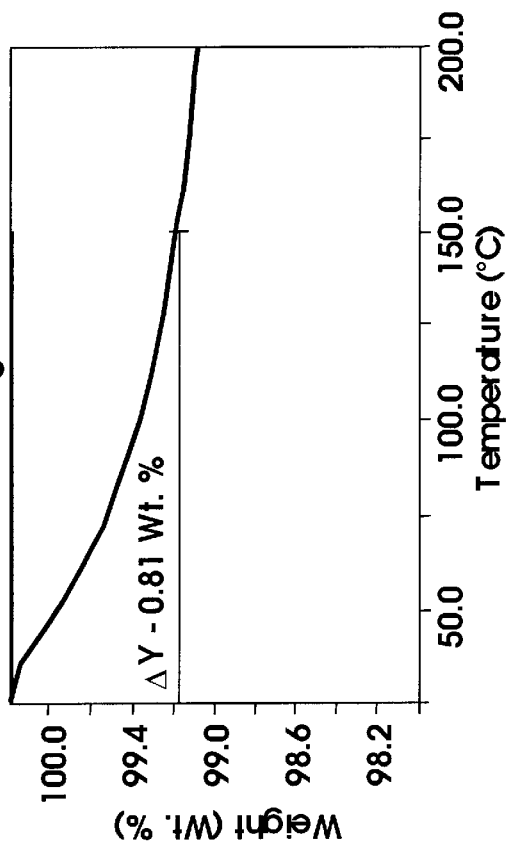
Figure 2B:
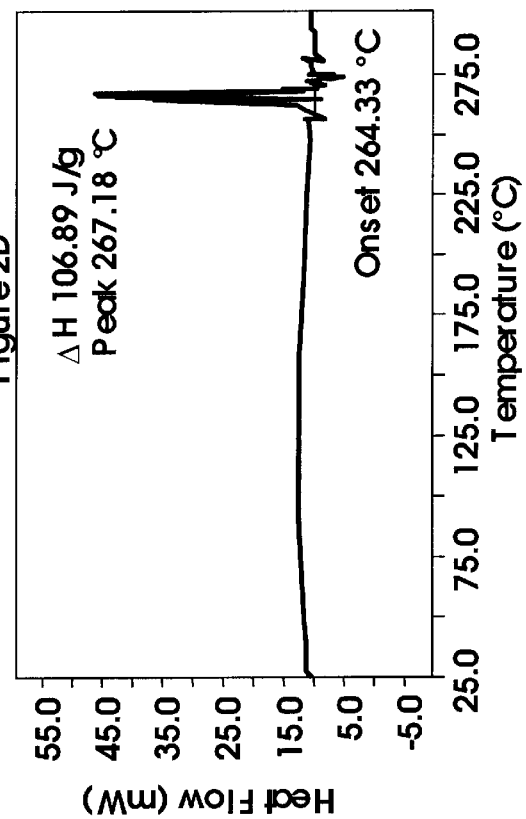

FIGS. 1B, 2B and 3B show, respectively, the thermogravimetric analysis (TGA), the differential scanning calorimetric (DSC) thermogram and the powder X-ray diffraction (XRD) patterns for the granulations of (E)-α-[2-n-butyl-1-[(4-carboxyphenyl)methyl]-1H-imidazol-5-yl]methylene-2-thiophenepropionic acid with Starch 1551 (96/4 eprosartan free base/Starch 1551).

Figure 1C:
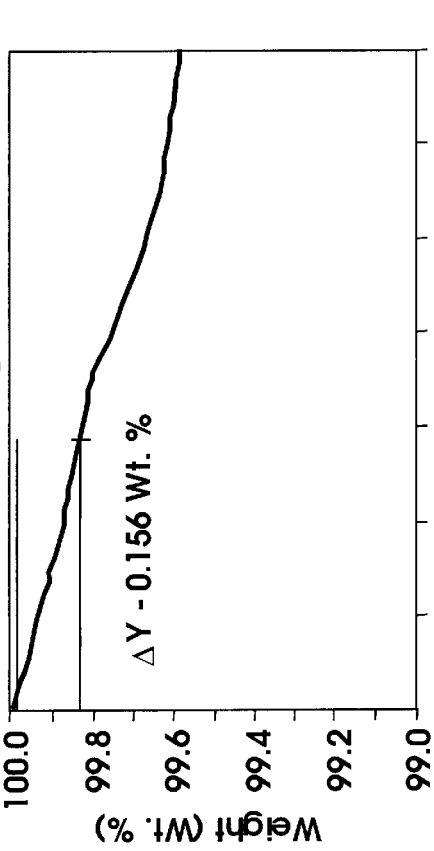
Figure 2C:
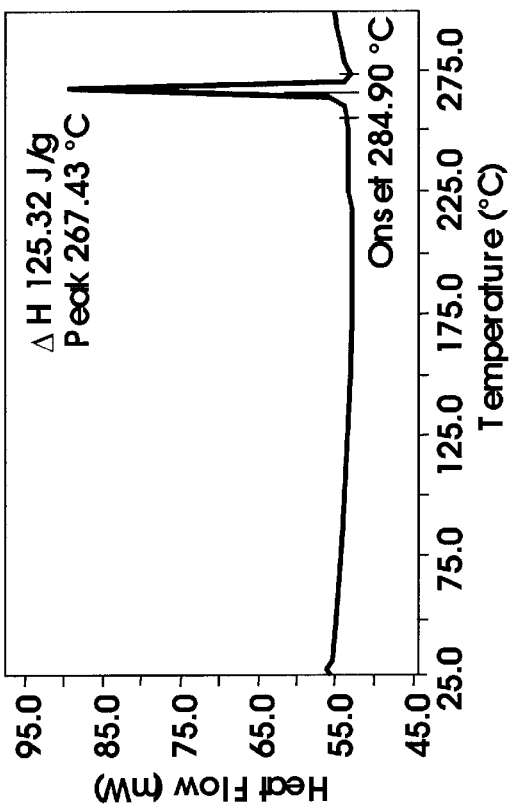

FIGS. 1C, 2C and 3C show, respectively, the thermogravimetric analysis (TGA), the differential scanning calorimetric (DSC) thermogram and the powder X-ray diffraction (XRD) patterns for the granulations of (E)-α-[2-n-butyl-1-[(4-carboxyphenyl)methyl]-1H-imidazol-5-yl]methylene-2-thiophenepropionic acid with L-arginine (95/5 eprosartan free base/L-arginine).

Figure 1D:
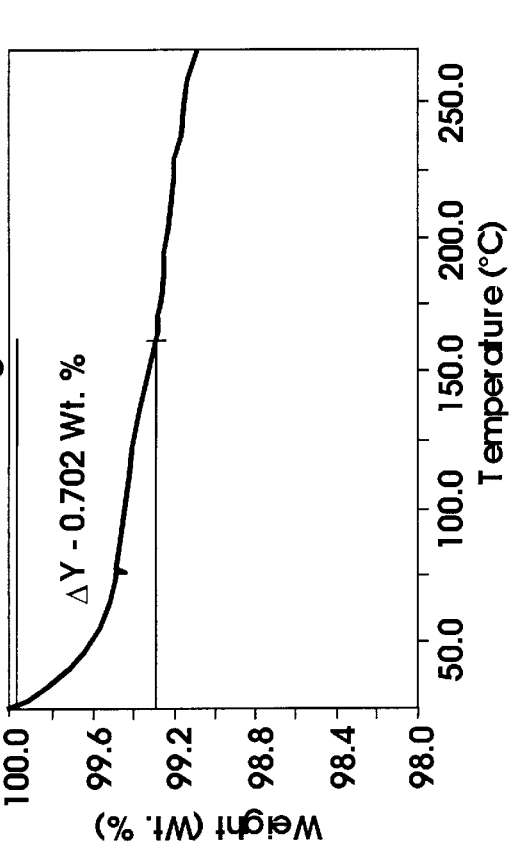
Figure 2D:
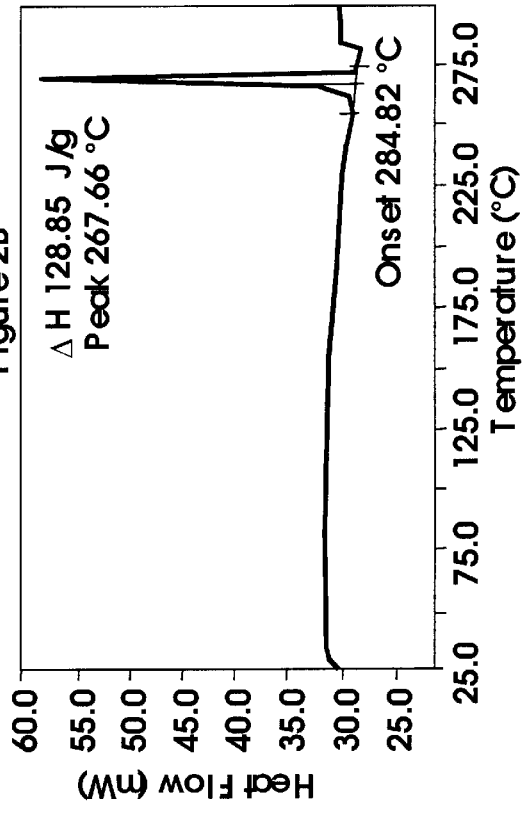

FIGS. 1D and 2D show, respectively, the thermogravimetric analysis (TGA) and the differential scanning calorimetric (DSC) thermogram for the granulations of (E)-α-[2-n-butyl-1-[(4-carboxyphenyl)methyl]-1H-imidazol-5-yl]

methylene-2-thiophenepropionic acid with Starch 1551, microcrystalline cellulose, hydrous lactose (88/4/4/4 eprosartan free base/Starch 1551/microcrystalline cellulose/hydrous lactose).

FIG. 3D shows the powder X-ray diffraction (XRD) patterns for the granulations of (E)-α-[2-n-butyl-1[(4-carboxy-phenyl)methyl]-1H-imidazol-5-yl]methylene-2-thiophenepropionic acid with Povidone (PVP) (96/4 eprosartan free base/PVP). These figures illustrate that, unlike the mesylate salt form, the free base of (E)-α-[2-n-butyl-1-[(4-carboxyphenyl)methyl]-1H-imidazol-5-yl]methylene-2-thiophenepropionic acid does not form a hydrate during wet granulation.

DETAILED DESCRIPTION OF THE INVENTION (E)-α-[2-n-Butyl-1-[(4-carboxyphenyl)methyl]-1H-imidazol-5-yl]methylene-2-thiophenepropionic acid is known to exist in an anhydrous form. This compound has the following structure:

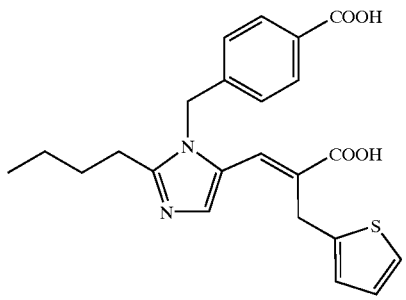

(E)-α-[2-n-Butyl-1-[(4-carboxyphenyl)methyl]-1H-imidazol-5-yl]methylene-2-thiophenepropionic acid, eprosartan, is claimed in U.S. Pat. No. 5,185,351. Reference should be made to said patent for its full disclosure, including the methods of preparing and using this compound. The entire disclosure of the '351 patent is incorporated herein by reference.

By immediate release formulation is meant any formulation such that by the time eposartan leaves the stomach, it is either in solution or it is in the form of a suspension of fine particles, i.e., a form from which eposartan can be readily absorbed.

By modified release is meant a controlled release or a delayed release formulation. By controlled release is meant any formulation that achieves slow release of drug over an extended period of time. In the controlled release formulations of the instant invention, a portion of the eposartan in the formulation is made available as a priming dose and the remainder is released in a sustained fashion. An example of a controlled release system is a matrix formulation. By delayed release is meant any formulation that utilizes repetitive, intermittent dosings of eposartan from one or more immediate release units incorporated into a single dosage form. Examples of delayed release systems include repeat action tablets and capsules, and enteric-coated tablets where timed release is achieved by a barrier coating.

Examples of controlled release formulations which are suitable for incorporating eprosartan are described in:
Sustained Release Medications, Chemical Technology, Review No. 177, Ed. J. C. Johnson, Noyes Data Corporation (1980); and
Controlled Drug Delivery, Fundamentals and Applications, 2nd Edition, Eds. J. R. Robinson, V. H. L. Lee, Mercel Dekkes Inc., New York (1987).

Examples of delayed release formulations which are suitable for incorporating eprosartan are described in:
Remington's Pharmaceutical Sciences, 16th Edition, Ed. A. Osol, Mack Publishing Company (1980).

Other examples of controlled release formulations which are suitable for incorporating eprosartan are described in U.S. Pat. No. 4,839,177, issued Jun. 13, 1989, and U.S. Pat. No. 5,422,123, issued Jun. 6, 1995. Matrix controlled release formulations for eprosartan are detailed in U.S. Pat. No. 4,389,393, issued Jun. 21, 1983, and U.S. Pat. No. 4,968,508, issued Nov. 6, 1990.

Eprosartan is an amphiphilic molecule containing two acidic (allylic carboxylic acid and phenylic carboxylic acid) and one basic (imidazole) functional groups. At lower pH (below 2) the imidazole nitrogen will be protonated (form ii). As the pH increases, the allylic carboxylic group will be deprotonated (form iii). Estimated $pK_a$ of the allylic carboxilic group is 2.9. As the pH increases further, the phenylic carboxylic group will be depronated (form iv) followed by the deprotonation of the protonated imidazole group (form v). The estimated $pK_a$ of the phenylic carboxylic group is 5.9 and that of imidazole group is 6.8. According to the pH-partitioning theory of absorption, only the unionized species (form ii) or the ion-neutral species (form iii) will be absorbed by passive diffusion.

According to the instant invention, eprosartan is suitably in the form of the free base in anydrous form. Eprosartan as the free base is a zwitterion or dipolar ion, since an acidic group and a basic group are part of the same molecule and in a neutral environment this compound exists as a dipolar ion.

Human clinical studies indicate that (E)-α-[2-n-butyl-1-[(4-carboxyphenyl)methyl]-1H-imidazol-5-yl]methylene-2-thiophenepropionic acid or its monomethanesulfonate salt is safe and well tolerated, even up to doses of 800 mg per day. The time to maximum concentration is between 1 to 2.5 hours in the fasted state and 2.5 to 4 hours in the fed state. (E)-α-[2-n-Butyl-1-[(4-carboxyphenyl)-methyl]-1H-imidazol-5-yl]methylene-2-thiophenepropionic acid monomethanesulfonate exhibits a mean absolute bioavailability of approximately 13%. As a result, doses of up to 800 mg per day may be required for treatment of hypertension, congestive heart failure and renal failure. Since (E)-α-[2-n-butyl-1-[(4-carboxy-phenyl)methyl]-1H-imidazol-5-yl] methylene-2-thiophenepropionic acid is formulated currently starting from its methanesulfonic acid in anhydrous form, which then forms a dihydrate in the wet granulation process, tablets are prepared for commercial use in which the load of active ingredient to total tablet weight is in a ratio of about 1:2 (w/w). For example, a tablet containing 600 mg of active ingredient weighs 1,200.0 mg.

It has been found that the free base of anhydrous eprosartan does not form a hydrate during wet granulation. Thus, this form of the compound is useful in the preparation of high drug load granules and high drug load tablets in which drug loads of about 70%, most preferably drug loads exceeding 85%, are produced. For example, a tablet containing 600 mg of active ingredient weighs about 860 mg. Most preferably, a tablet containing 600 mg of active ingredient weighs about 660 mg.

In accordance with the present invention, it has been found that stable high drug load tablet formulations of (E)-α-[2-n-butyl-1-[(4-carboxyphenyl)methyl]-1H-imidazol-5-yl]methylene-2-thiophenepropionic acid are produced by wet granulation processing of the anhydrous form of said compound with water in the presence of pharmaceutically acceptable excipients, for example, binders, such as corn starch, pregelatinized starch [Starch 1551], polyvinylpyrrolidone (PVP), gelatin, low molecular weight hydroxypropylmethylcellulose (HPMC), or hydroxypropylcellulose (HPC), methylcellulose and L-arginine. Granules by dry granulation processing are produced, for example, by slugging or roller compacting, milling and sieving, of the anhydrous form of (E)-α-[2-n-butyl-1-[(4-carboxyphenyl)methyl]-1H-imidazol-5-yl]methylene-2-thiophenepropionic acid in the presence of pharmaceutically acceptable excipients.

The high drug load granules of anhydrous (E)-α-[2-n-butyl-1-[(4-carboxyphenyl)methyl]-1H-imidazol-5-yl] methylene-2-thiophenepropionic acid formed during the wet granulation process are prepared using a planetary/high shear/fluid bed granulator for preparing solid dosage forms of the anhydrous form of said compound with water in the presence of binder. A slugging press or a roller compactor can also be used to prepare dry granules to be incorporated into oral solid dosage forms.

The drug substance using either a wet or a dry granulation process does not form a hydrate, and it does not form a hydrate during storage of its oral solid dosage forms. Any combination of pharmaceutically acceptable excipients, e.g. diluents, fillers, binders and disintegrants, in desired proportions may be utilized in accordance with the wet or dry granulation process of the present invention. The excipients commonly used in pharmaceutical industry are well described in the literature [refer to the Handbook of Pharmaceutical Excipients, A. Wade and P. J. Weller (Editors), American Pharmaceutical Association (1994)]. Pharmaceutically acceptable fillers and diluents include, but are not limited to, the following: lactose (hydrous as well as anhydrous), starch [unmodified (corn starch) or modified (for example, Starch 1500 available from Colorcon)], mannitol, sorbitol, cellulose, inorganic sulfates and phosphates. Disintegrants include, but are not limited to, the following: sodium starch glycolate, sodium carmellose and crosslinked polyvinyl pyrrolidone, and binders include, but are not limited to, the following: gelatin, corn starch, modified starch (Starch 1551, pregelatinized starch), hydroxypropyl methyl cellulose (HPMC), hydroxypropyl cellulose (HPC), sodium carboxy methyl cellulose, alginic acid, acacia and amino acids, such as glycine and L-arginine. Examples of excipients suitable for modified release applications include, but are not limited to, the following: high molecular weight HPMCs, polymethacrylate polymers known as Eudragits, polyethylene oxide, Polyox® (Union Carbide Corporation), modified ethyl cellulose, Surelease® (Colorcon), crosslinked acrylic acid polymers, Carbopol® (BF Goodrich Speciality Chemicals) and waxy materials, such as glyceryl behenate (Compritol®), glyceryl palmitostearate (Precirol®), and Gelucires® [all from Gattefosse s.a., France] and carnauba wax.

Preferably, the pharmaceutically acceptable excipients used as binders, diluents and fillers during the wet granulation process of this invention are lactose, mannitol, sorbitol, starch (corn starch, soluble starch, or Starch 1551), gelatin, xanthan gum, sodium alginate, Povidone (PVP), and microcrystalline or powdered cellulose, each one of which may act as a facilitator in the formation of a stable high drug load solid dosage form of eprosartan. More preferably, the excipients are lactose, Starch 1551, microcrystalline cellulose, Povidone (PVP), and arginine. Most preferably, the excipients are lactose, cellulose and Starch 1551 or arginine.

Preferably, the excipients used in the wet or dry granulation process are present in 0–25% on a weight for weight basis. Most preferably, the excipients may be present at as low as 0–15% on a weight for weight basis in order to produce granulations with a high drug load.

The process for preparing the solid dosage forms in accordance with the present invention may be carried out using a combination of a planetary mixture, a V-blender, a high shear granulator, a fluid bed granulator, a slugging press, a roller compactor, a cummunuting mill, sieving equipment, or a tableting machine. Optionally, the granulation of the anhydrous form of (E)-α-[2-n-butyl-1-[(4-carboxyphenyl)methyl]-1H-imidazol-5-yl]methylene-2-thiophenepropionic acid, produced using a conventional dry or wet granulating equipment, is suitable for the preparation of immediate or modified release dosage forms. Optionally, the dry or granulation of 1:1 molar or 1:1 w/w of (E)-(X-[2-n-butyl-1-[(4-carboxyphenyl)methyl]-1H-imidazol-5-yl] methylene-2-thiophenepropionic acid, produced using a conventional dry or wet granulating equipment, is suitable for the preparation of immediate or modified release dosage forms immediate release tablet cores may be coated with a membrane of a polymer imparting delayed or sustained release properties.

Thus, the present invention provides a pharmaceutical composition which comprises (E)-α-[2-n-butyl-1-[(4-carboxyphenyl)methyl]-1H-imidazol-5-yl]methylene-2-thiophenepropionic acid and a pharmaceutically acceptable carrier. The pharmaceutical composition is adapted for oral administration. The composition is presented as a unit dose pharmaceutical composition containing from about 50 mg to about 1.0 g of (E)-α-[2-n-butyl-1-[(4-carboxyphenyl) methyl]-1H-[imidazol-5-yl]methylene-2-thiophenepropionic acid, preferably from about 200 to about 400 mg. Such a composition is normally taken from 1 to 4 times daily, preferably from 1 to 2 times daily. The preferred unit dosage forms include tablets or capsules. The compositions of this invention may be formulated by conventional methods of admixture such as blending, filling and compressing. Suitable pharmaceutically acceptable carriers for use in this invention include diluents, fillers, binders and disintegrants.

(E)-α-(2-n-Butyl-1-[(4-carboxyphenyl)methyl]-1H-imidazol-5-yl]methylene-2-thiophenepropionic acid may be co-administered with other pharmaceutically active compounds, for example, in physical combination or by sequential administration. Conveniently, the compound of this invention and the other active compound are formulated in a pharmaceutical composition. Thus, this invention also relates to pharmaceutical compositions comprising (E)-α-[2-n-butyl-1-[(4-carboxyphenyl)methyl]-1H-imidazol-5-yl] methylene-2-thiophenepropionic acid, a pharmaceutically acceptable carrier, and a second pharmaceutically active compound selected from the group consisting of a diuretic, a calcium channel blocker, a β-adrenoceptor blocker, a renin inhibitor, and an angiotensin converting enzyme inhibitor. Examples of compounds which may be included in pharmaceutical compositions in combination with (E)-α-[2-n-butyl-1-[(4-carboxyphenyl)methyl]-1H-imidazol-5-yl] methylene-2-thiophenepropionic acid are diuretics, particularly a thiazide diuretic, such as hydrochlorothiazide, or a loop diuretic, such as furosemide, calcium channel blockers, particularly dihydropyridine antagonists, such as nifedipine, β-adrenoceptor blockers, such as propranolol, renin inhibitors, such as enalkinen, and angiotensin converting enzyme inhibitors, such as captopril or enalapril. Preferably, the pharmaceutical composition contains 200–400 mg of (E)-α-[2-n-butyl-1-[(4-carboxyphenyl)-methyl]-1H-imidazol-5-yl]methylene-2-thiophene-propionic acid in combination with 6.25–25 mg of hydrochlorothiazide.

No unacceptable toxicological effects are expected when (E)-α-[2-n-butyl-1-[(4-carboxyphenyl)methyl]-1H-imidazol-5-yl]methylene-2-thiophenepropionic acid is administered in accordance with the present invention.

(E)-α-[2-n-Butyl-1-[(4-carboxyphenyl)methyl]-1H-imidazol-5-yl]methylene-2-thiophenepropionic acid is useful for treating diseases in which blockade of the angiotensin II receptor would be beneficial. Preferably, this compound is used alone or in combination with said second pharmaceutically active compounds in the treatment of hypertension, congestive heart failure and renal failure. Additionally, (E)-α-[2-n-butyl-1-[(4-carboxyphenyl)methyl]-1H-imidazol-5-yl]methylene-2-thiophenepropionic acid is of value in the treatment of left ventricular hypertrophy regression, diabetic nephropathy, diabetic retinopathy, mascular degeneration, haemorrhagic stroke, primary and secondary prevention of infarction, prevention of atheroma progression and the regression of atheroma, prevention of restinosis after angioplasty or bypass surgery, improving cognitive function, angina, glaucoma, and CNS disorders, such as anxiety.

The following examples are illustrative of the instant invention. These examples are not intended to limit the scope of this invention as defined hereinabove and as claimed hereinbelow.

In Examples 1–7, below, the term "internal granules" means the granulation obtained by blending and granulating ingredients (drug substance and excipients) by a wet or dry granulation process.

EXAMPLES

Example 1

96.0 parts of Eprosartan and 4.0 parts of pregelatinized starch (Starch 1551), a binder are granulated in a planetary mixer using purified water as the granulating agent The moist granulation is wet milled and dried using a fluid bed drier or an appropriate drying device. The dried granulation is milled to produce granules passing through a #30 mesh or appropriate size sieve. Compression mixes with ingredients as listed in Formulas 1 and 2 are prepared by blending and compressed into 300 mg tablets with a tensile strength in the range of 1.5–2.2 Mpa (8–13 kP) using a tablet press. Tablets of Formulas 1 and 2 disintegrate in less than 2 minutes when tested in purified water at 37° C.

| Ingredients (%) | Formula 1 | Formula 2 |
|---|---|---|
| Internal granules | 95.42 | 89.29 |
| Microcrystalline cellulose | — | 5.71 |
| Crospovidone, crosslinked PVP | 3.82 | 4.00 |
| Magnesium stearate | 0.76 | 1.00 |
| Total | 100.0 | 100.0 |

Example 2

95.0 parts of Eprosartan and 5.0 parts of L-Arginine, a binder are granulated in a high shear granulator using purified water as the granulating agent. The moist granulation is wet milled using a Fitzmill and dried using a tray drier or an appropriate drying device. The dried granulation is milled to produce granules passing through a #30 mesh or appropriate size sieve. Compression mixes with ingredients as listed in Formulas 3 and 4 are prepared by blending and compressed into 300 mg tablets of hardness in the range of 7–10 kP using a tablet press (disintegration time: 10–16 minutes):

| Ingredients (%) | Formula 3 | Formula 4 |
|---|---|---|
| Internal granules | 95.41 | 90.23 |
| Microcrystalline cellulose | — | 5.00 |
| Crospovidone, crosslinked PVP | 3.84 | 4.00 |
| Magnesium stearate | 0.75 | 0.77 |
| Total | 100.0 | 100.0 |

Example 3

86.0 parts of Eprosartan, 4.0 parts microcrystalline cellulose (Avicel PH102), 4.0 parts hydrous lactose, 2.0 parts crosslinked polyvinylpyrrolidone (Crospovidone) and 4.0 parts of pregelatinized starch (Starch 1551), a binder are granulated in a planetary mixer using purified water as the granulating agent. The moist granulation is wet milled and dried using a fluid bed drier or an appropriate drying device. The dried granulation is milled to produce granules passing through a #30 mesh or appropriate size sieve. A compression mixes with ingredients as listed in Formula 5 is prepared by blending and compressed in 300 mg tablets (tablet weight: 400 mg) of hardness in the range of 5–10 kP using a tablet press:

| Ingedients | Formula 5 |
|---|---|
| Granules | 87.2 |
| Microcrystalline cellulose | 10.0 |
| Ac-Di-Sol, sodium croscarmellose | 2.0 |
| Magnesium stearate | 0 8 |
| Total | 100.0 |

Example 4

92.0 parts of Eprosartan and 4.0 parts of L-Arginine or PVP, 2% Crospovidone, and 2% glyceryl behenate (Compritol) are blended, roller compacted, milled using a Fitzmill milled to produce granules passing through a #30 mesh or appropriate size sieve. Compression mixes with ingredients as listed in Formulas 6 and 7 are prepared by blending and compressed into 200 mg tablets of hardness in the range of 4–10 kP using a tablet press:

| Ingredients (%) | Formula 6 (L-Arginine) | Formula 7 (PVP) |
|---|---|---|
| Internal granules | 89.34 | 86.96 |
| Microcrystalline cellulose | 6.97 | 9.24 |
| Crospovidone, crosslinked PVP | 3.01 | 3.00 |
| Magnesium stearate | 0.68 | 0.80 |
| Total | 100.0 | 100.0 |

Modified Release Formulations

Example 5

70.8 parts of Eprosartan and 29.2 parts L-arginine are granulated in a high shear granulator using purified water as the granulating agent. The moist granulation is wet milled and dried using a fluid bed drier or an appropriate drying device. The dried granulation is milled to produce granules passing through a #30 mesh or appropriate size sieve. In another prototype development, 50 parts of Eprosartan and 50 parts of L-arginine are granulated using a fluid bed granulator, and the fluid bed dried granules are milled to produce granules passing through a #30 mesh or appropriate sieve. Compression mixes with ingredients as listed in Formulas 8 and 9 are prepared by blending and compressed into 50 mg tablets (tablet weight: 85 and 120 mg, respectively) of appropriate hardness using a tablet press:

| Ingredients (mg) | Formula 8 | Formula 9 |
|---|---|---|
| Granules | 70.6 | 100.0 |
| Microcrystalline cellulose | 10.1 | 14.0 |
| Crospovidone | 3.6 | 5.0 |
| Magnesium stearate | 0.7 | 1.0 |
| Total | 85.0 | 120.0 |

Example 6

47 parts of Eprosartan, 47 parts L-Arginine, 2% Crospovidone and 3% glyceryl behenate (Compritol) are blended, roller compacted, milled using a Fitzmill milled to produce granules passing through a #30 mesh or appropriate size sieve. In another variation of the formulation, 67.4 parts of Eprosartan, 27.8 parts L-Arginine, 1.9% Crospovidone and 2.9% glyceryl behenate (Compritol) are blended, roller compacted, milled using a Fitzmill milled to produce granules passing through a #30 mesh or appropriate sieve. Compression mixes with ingredients as listed in Formulas 10 and 11 are prepared by blending and compressed into 200 mg tablets of hardness in the range of 8–14 kP using a rotary tablet press:

| Ingredients (mg) | Formula 10 (1:1 w/w) | Formula 11 (1:1 Mole) |
|---|---|---|
| Internal granules | 425.5 | 296.7 |
| Microcrystalline cellulose | 41.0 | 32.0 |
| Crospovidone, crosslinked PVP | 10.0 | 14.0 |
| Magnesium stearate | 3.5 | 2.3 |
| Total | 480.0 | 345.0 |

Example 7

96.0 parts of Eprosartan and 4.0 parts of Starch 1551 are granulated in a high shear granulator. Compression mixes with ingredients as listed in Formulas 12 and 13 are prepared by blending and compressed into 200 mg tablets using an a tablet press

| Ingredients (%) | Formula 12 (1:1 Molar) | Formula 13 (1:2 Molar) |
|---|---|---|
| Internal granules | 208.3 | 208.3 |
| L-arginine | 82.7 | 165.0 |
| Microcrystalline cellulose | 41.3 | 42.7 |
| Crospovidone, crosslinked PVP | 15.0 | 20.0 |
| Magnesium stearate | 3.0 | 4.0 |
| Total | 350.0 | 440.0 |

Film Coating:

Tablets of Formulas 1–4 may be optionally provided with an aqueous film coating. Generally, these tablets are coated first with a polymer solution to form a clear film, and then coated with an aqueous polymer solution/suspension to form an opaque, white or colored film. This film coating does not have any effect on the disintegration of the tablet, and hence, the drug dissolution is not affected. In contrast, tablets of Formulas 5–7 are first coated with an aqueous polymer solution to form a clear film (often called seal coat) and then with an aqueous solution/suspension of an enteric polymer such as Eudragit L30D, hydroxypropyl methylcellulose acetate phthalate (HPMCP), cellulose acetate phthalate (CAP) or polyvinyl acetate phthalate (PVAP). The weight gains following seal coat and enteric coat are about 3–6% and 4–12% (most preferably 3–4% and 4–6%) respectively. The modified release tablets thus produced release <20% drug in the stomach following the oral administration and rapidly release the drug at higher pHs, depending on the polymer used (for e.g., at a pH >4.0 for PVAP, >5.0 for HPMCP and 5.5 for Eudragit), even though the drug solubility at these initiation pHs is negligible. The water imbibed into the tablets dissolves arginine creating a high pH environment in which Eprosartan dissolves. This high pH also dissolves the film coating, releasing the drug substance to the environment.

It is to be understood that the invention is not limited to the embodiments illustrated herein above and the right is reserved to the illustrated embodiments and all modifications coming within the scope of the following claims.

The various references to journals, patents, and other publications which are cited herein comprise the state of the art and are incorporated herein by reference as though fully set forth.

What is claimed is:

1. A wet or dry granulation of high drug load anhydrous (E)-α-[2-n-butyl-1-[(4-carboxyphenyl)methyl]-1H-imidazol-5-yl]methylene-2-thiophenepropionic acid.

2. A high drug load formulation comprising anhydrous (E)-α-[2-n-butyl-1-[(4-carboxyphenyl)methyl]-1H-imidazol-5-yl]methylene-2-thiophenepropionic acid in oral dosage unit form.

3. A high drug load immediate release formulation comprising anhydrous (E)-α-[2-n-butyl-1-[(4-carboxyphenyl)methyl]-1H-imidazol-5-yl]methylene-2-thiophenepropionic acid in oral dosage unit form.

4. A high drug load modified release formulation comprising anhydrous (E)-α-[2-n-butyl-1-[(4-carboxyphenyl)methyl]-1H-imidazol-5-yl]methylene-2-thiophenepropionic acid in oral dosage unit form.

5. A process for preparing a high drug load formulation of anhydrous (E)-α-[2-n-butyl-1-[(4-carboxyphenyl)methyl]-1H-imidazol-5-yl]methylene-2-thiophenepropionic acid in which a wet or dry granulation of high drug load anhydrous (E)-α-[2-n-butyl-1-[(4-carboxyphenyl)methyl]-1H-imidazol-5-yl]methylene-2-thiophenepropionic acid is prepared in the presence of water and pharmaceutically acceptable excipients.

6. A process for preparing a high drug load formulation of anhydrous (E)-α-[2-n-butyl-1-[(4-carboxyphenyl)methyl]-1H-imidazol-5-yl]methylene-2-thiophenepropionic acid in which a wet granulation of high drug load anhydrous (E)-α-[2-n-butyl-1 -[(4-carboxyphenyl)methyl]-1H-imidazol-5-yl]methylene-2-thiophenepropionic acid is prepared in the presence of water and pharmaceutically acceptable excipients.

7. A process for the preparation of a granulation of a high drug load anhydrous (E)-α-[2-n-butyl-1-[(4-carboxyphenyl)methyl]-1-H-imidazol-5-yl]methylene-2-thiophenepropionic acid which comprises:

(i) mixing the anhydrous form of (E)-α-[2-n-butyl-1-[(4-carboxyphenyl)-methyl]-1H-imidazol-5-yl]methylene-2-thiophenepropionic acid and pre-gelatinized starch, with optionally one or more pharmaceutically acceptable excipients; and (ii) granulating the mixture with water.

8. A process for the preparation of a granulation of a high drug load anhydrous (E)-α-[2-n-butyl-1-[(4-carboxyphenyl)methyl]-1H-imidazol-5-yl]methylene-2-thiophene-propionic acid which comprises:

(i) mixing the anhydrous form of (E)-α-[2-n-butyl-1-[(4-carboxyphenyl)methyl]-1H-imidazol-5-yl]methylene-2-thiophenepropionic acid and L-arginine, optionally with one or more pharmaceutically acceptable excipients; and (ii) granulating the mixture with water.

9. A process for the preparation of a granulation of a high drug load anhydrous (E)-α-[2-n-butyl-1-[(4-carboxyphenyl)methyl]-1H-imidazol-5-yl]methylene-2-thiophene-propionic acid which comprises:

(i) blending the anhydrous form of(E)-α-[2-n-butyl-1-[(4-carboxy-Phenyl)methyl]-1H-imidazol-5-yl]methylene-2-thiophenepropionic acid, pregelatinized starch with one or more pharmaceutically acceptable excipients selected from crosslinked polyvinyl pyrrolidone and glyceryl behenate;

(ii) slugging or roller compacting the blend; and (iii) milling and sieving the granulation.

10. A process for the preparation of an oral dosage form anhydrous (E)-α-[2-n-butyl-1-[(4-carboxyphenyl)methyl]-1H-imidazol-5-yl]methylene-2-thiophene-propionic acid which comprises:

(i) producing high drug load granules containing (E)-α-[2-n-butyl-1-[(4-carboxy-phenyl)methyl]-1H-imidazol-5-yl]methylene-2-thiophenepropionic acid and a binder; and (ii) blending said granules with other pharmaceutically acceptable excipients to be compressed into a tablet.

11. A process for the preparation of a modified release oral dosage form of anhydrous (E)-α-[2-n-butyl-1[(4-carboxyphenyl)methyl]-1H-imidazol-5-yl]methylene-2-thiophene-propionic acid which comprises:

(i) producing high drug load granules of anhydrous form of (E)-α-[2-n-butyl-1-[(4-carboxy-phenyl)methyl]-1H-imidazol-5-yl]methylene-2-thiophenepropionic acid and L-arginine in a 1:1 molar or 1:1 w/w ratio by a wet or dry granulation process; and (ii) blending said granules with other pharmaceutically acceptable excipients to be compressed into a tablet.

12. A process for the preparation of a modified release oral dosage form of anhydrous (E)-α-[2-n-butyl 1-[(4-carboxyphenyl)methyl ]-1H-imidazol-5-yl]methylene-2-thiophene-propionic acid which comprises:

(i) producing high drug load granules of anhydrous form of (E)-α-[2-n-butyl-1-[(4-carboxy-phenyl)methyl]-1H-imidazol-5-yl]methylene-2-thiophenepropionic acid and Starch 155;

(ii) blending said granules and L-arginine in a 1:1 molar or 1:1 w/w ratio; and (iii) blending said blend optionally with other pharmaceutically acceptable excipients to be compressed into a tablet.

13. A method of blocking angiotensin II receptors which comprises administering to a subject in need thereof an effective amount of a high drug load formulation of anhydrous (E)-α-[2-n-butyl-1-[(4-carboxyphenyl)methyl]-1H-imidazol-5-yl]methylene-2-thiophene-propionic acid.

14. A method of treating hypertension which comprises administering to a subject in need thereof an effective amount of a high drug load formulation of anhydrous (E)-α-[2-n-butyl-1-[(4-carboxyphenyl)methyl]-1H-imidazol-5-yl]methylene-2-thiophene-propionic acid.

15. A method of treating hypertension which comprises administering stepwise or in physical combination a high drug load granulation of anhydrous (E)-α-[2-n-butyl-1-[(4-carboxyphenyl)methyl]-1H-imidazol-5-yl]methylene-2-thiophene-propionic acid and a second pharmaceutically active compound selected from the group consisting of a diuretic, a calcium channel blocker, a β-adrenoceptor blocker, a renin inhibitor, and an angiotensin converting enzyme inhibitor.

16. The method according to claim 15 wherein the second pharmaceutically active compound is a diuretic.

17. The method according to claim 16 wherein the diuretic is hydrochlorothiazide.

18. The method according to claim 15 wherein the second pharmaceutically active compound is a loop diuretic.

19. The method of claim 18 wherein the loop diuretic is furosemide.

20. A method of treating congestive heart failure which comprises administering to a subject in need thereof an effective amount of a high drug load formulation of anhydrous (E)-α-[2-n-butyl-1-[(4-carboxyphenyl)methyl]-1H-imidazol-5-yl]methylene-2-thiophene-propionic acid.

21. A method of treating renal failure which comprises administering to a subject in need thereof an effective amount of a high drug load formulation of anhydrous (E)-α-[2-n-butyl-1-[(4-carboxyphenyl)methyl]-1H-imidazol-5-yl]methylene-2-thiophene-propionic acid.

* * * * *